United States Patent
Steidl et al.

(12)

(10) Patent No.: US 6,342,302 B1
(45) Date of Patent: Jan. 29, 2002

(54) CERAMIC DENTAL RESTORATION

(75) Inventors: Jürgen Steidl, Wöllstadt; Steffen Assmann, Bad Nauheim, both of (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/438,537

(22) Filed: Nov. 12, 1999

(30) Foreign Application Priority Data

Nov. 13, 1998 (DE) .......................... 198 52 516

(51) Int. Cl.⁷ .............................. A61C 13/08; B32B 9/00
(52) U.S. Cl. ...................... 428/446; 428/697; 428/699; 428/701; 428/702; 501/6; 501/68; 106/35; 433/206; 433/212.1; 433/223
(58) Field of Search ........................ 428/446, 70, 76, 428/404, 697, 699, 701, 702; 433/218, 223, 212.1, 206; 501/6, 10, 68, 70; 106/35

(56) References Cited

U.S. PATENT DOCUMENTS

| 4,604,366 A | 8/1986 | Kacicz et al. |
|---|---|---|
| 4,798,536 A | 1/1989 | Katz |
| 5,614,330 A | 3/1997 | Panzera |
| 5,653,791 A | 8/1997 | Panzera |
| 5,698,019 A | * 12/1997 | Frank et al. |
| 5,705,273 A | 1/1998 | Denry et al. |

FOREIGN PATENT DOCUMENTS

| DE | 4031168 | 4/1992 |
|---|---|---|
| DE | 4423793 | 2/1996 |
| DE | 4423794 | 2/1996 |
| DE | 4428839 | 2/1998 |
| DE | 196 47 739 | 3/1998 |
| DE | 198 50 266 | 5/1999 |
| EP | 0 231 773 | 1/1987 |
| EP | 0231773 | 8/1987 |
| EP | 0622342 | 11/1994 |

OTHER PUBLICATIONS

JADA, vol. 128, Mar. 1997, "A Review of All–Ceramic Restorations", pp. 297–307.
Ivoclar–Vivadent Report, IPS–Empress: Eine Neue Keramik–Technologie, G. Behman, pp. 3–15.

* cited by examiner

*Primary Examiner*—Blaine Copenheaver
*Assistant Examiner*—Jennifer McNeil
(74) *Attorney, Agent, or Firm*—Smith, Gambrell & Russell, LLP

(57) ABSTRACT

A ceramic restoration based on a leucitic glass-ceramic, which is characterized in that the glass-ceramic includes by way of components

| 40–95 wt.-% | $SiO_2$ |
|---|---|
| 5–25 wt.-% | $Al_2O_3$ |
| 5–25 wt.-% | $K_2O$ |
| 0–25 wt.-% | $Na_2O$ |
| 0–20 wt.-% | $CaO$ |
| 0–8 wt.-% | $B_2O_3$ |
| 0–0.5 wt.-% | $P_2O_5$ |
| 0–3 wt.-% | F, | in that it contains, as sole crystalline phase, leucite in a total proportion from 20 to 45 wt.-%, at least 80% of the theoretically producible quantity of leucite being present, and in that it exhibits a linear coefficient of thermal expansion $\alpha_{(20-500° C.)}$ from $12.5 \cdot 10^{-6}$ to $15.5 \cdot 10^{-6}$ $K^{-1}$. This glass-ceramic is particularly suitable for processing as pressed ceramic and can be advantageously faced with dental ceramic that exhibits a linear coefficient of thermal expansion $\alpha_{(20-500° C.)}$ from $13.5 \cdot 10^{-6}$ to $17.0 \cdot 10^{-6}$ $K^{-1}$.

15 Claims, No Drawings

CERAMIC DENTAL RESTORATION

INTRODUCTION AND BACKGROUND

The present invention relates to a ceramic dental restoration based on a leucitic glass-ceramic which, in particular, can be obtained from a dental-ceramic material according to the invention being press-moulded in the viscous state into a shape corresponding to the dental restoration.

Dental restorations, such as artificial teeth, crowns, partial crowns, bridges, inlays, onlays, facets, stump reconstructions, tooth-root constructions etc., are predominantly manufactured from metal alloys, in particular from alloys based on precious metals. These metal alloys are usually faced for aesthetic reasons with ceramic, in order to give the restoration, particularly in the visible region, an appearance corresponding as far as possible to the natural tooth.

Facing-ceramics have to be very carefully matched as regards melting-point and coefficient of thermal expansion (CTE) to the material of the basic framework. In the case of metal-ceramic systems, ordinarily the CTE of the ceramic is chosen so that the coefficient lies slightly below that of the metallic base material. In this way, tensile stresses in the facing-ceramic are prevented and compressive stresses are induced instead, so that in the course of firing-on and cooling and also in the event of later loads as a result of fluctuation in temperature the occurrence of fissures is avoided. Facing-ceramics that are matched to the high gold containing dental alloys which have been dominant for a great many years by reason of better compatibility typically possess a linear CTE $\alpha_{(20\text{-}500°\ C.)}$ from about $12.5 \cdot 10^{-6}$ to about $16.5 \cdot 10^{-6}$ K$^{-1}$. Such ceramic materials are described in EP 0 478 937, for example. A facing-ceramic pertaining to this category which is frequently employed in practice exhibits a CTE $\alpha_{(20\text{-}500°\ C.)}$ of $15.0 \cdot 10^{-6}$ K$^{-1}$.

As an alternative to metal-ceramic dental restorations, fully ceramic systems are being employed on an increasing scale. By way of base materials, use is predominantly made of glass-ceramics in this case. Materials are designated as glass-ceramics in which at least one crystalline phase is present in a distributed manner in a glass phase. Glass-ceramic may be obtained from an amorphous primary glass being subjected to a controlled partial crystallization process.

In U.S. Pat. No. 4,798,536, for example, fully ceramic dental restorations consisting of glass-ceramic based on feldspar are described, said restorations containing at least 45 wt.-% leucite by way of crystalline phase. In this case the dental product is shaped using slip technology and then sintered.

A technology for the manufacture of fully ceramic dental restorations has proved particularly advantageous in which a suitable dental-ceramic material is converted into the viscous state under the influence of high temperature and under pressure and is press-moulded into a shape corresponding to the dental restoration. Such a material, as well as the dental product produced therefrom, is also frequently designated in dental technology as pressed ceramic. This technology and a pressing furnace suitable for it are described in EP 0 231 773 A1.

In DE 44 23 793 C1 a dental glass-ceramic which is capable of being processed as pressed ceramic is described which contains leucite and at least one other crystalline phase.

In DE 44 23 794 C1 a dental glass-ceramic which is also capable of being processed as pressed ceramic is described which contains, by way of crystalline phase, $ZrO_2$ and at least one other crystalline phase.

In DE 196 47 793 A1 a dental glass-ceramic which is capable of being processed as pressed ceramic is described which contains lithium disilicate by way of crystalline phase.

The known glass-ceramics based on leucite that are employed in practice as pressed ceramic exhibit a CTE $\alpha_{(20\text{-}500°\ C.)}$ which, as a rule, lies in the range from about $14 \cdot 10^{-6}$ to about $20 \cdot 10^{-6}$ K$^{-1}$, and should therefore be capable of being combined with the conventional facing-ceramics having a low CTE.

In practice, however, it has been shown that the manufacture of fully ceramic dental restorations by combining these known glass-ceramics by way of framework material with the facing-ceramics that are used in metal-ceramic systems leads to problems, despite the similar matching of the coefficients of thermal expansion. For instance, in the course of facing work a high reject-rate is observed as a result of cracking. Fluctuating-temperature loads result, to an unacceptable degree, in further cracking and failure as a result of fracture. Furthermore, in the course of the multiple firings which are usually required in practice a drifting of the CTE of the glass-ceramic parent substance towards higher values is observed, which again favours formation of fissures and fracture.

An object of the invention was therefore to develop a glass-ceramic for the manufacture of ceramic dental restorations with which the problems that have been described do not arise in the course of facing with currently available facing-ceramics.

The above and other objects of the invention can be achieved if, in the case of ceramic dental restorations by way of base material, a leucitic glass-ceramic is employed which is characterized in that it comprises

| | |
|---|---|
| 40–95 wt.-% | $SiO_2$ |
| 5–25 wt.-% | $Al_2O_3$ |
| 5–25 wt.-% | $K_2O$ |
| 0–25 wt.-% | $Na_2O$ |
| 0–20 wt.-% | $CaO$ |
| 0–8 wt.-% | $B_2O_3$ |
| 0–0.5 wt.-% | $P_2O_5$ |
| 0–3 wt.-% | F, | and, as the sole crystalline phase, leucite in a total proportion of 20–45 wt.-%, at least 80% of the theoretically producible quantity of leucite being present, and which exhibits a linear coefficient of thermal expansion $\alpha_{(20\text{-}500°\ C.)}$ from $12.5 \cdot 10^{-6}$ to $15.5 \cdot 10^{-6}$ K$^{-1}$.

The present invention consequently provides a ceramic dental restoration based on a leucitic glass-ceramic which is described above.

In a further aspect, the invention provides a process for manufacturing a ceramic dental restoration based on leucitic glass-ceramic wherein a glass-ceramic which is described above is press-moulded in the viscous state into a shape corresponding to the dental restoration.

The invention is based on the surprising discovery that in the case of fully ceramic dental restorations it is advantageous, with a view to avoiding cracking and consequential damage, to have the CTE of the base ceramic, in contrast with the tried and tested situation in the case of metal-ceramic systems, to be lower than that of the facing-ceramic. In the case of leucitic glass-ceramic the CTE is dependent on the content of leucite, the pure glass phase exhibiting a CTE $\alpha_{(20\text{-}500°\ C.)}$ of about $10\cdot10^6\ K^{-1}$ and the pure tetragonal leucite exhibiting a CTE $\alpha_{(20\text{-}500°\ C.)}$ of about $20\cdot10^{-6}\ K^{-1}$. Leucite, $K[AlSi_2O_6]$, may be formed by crystallization in a primary glass if the latter contains the components $SiO_2$, $Al_2O_3$ and $K_2O$.

The glass-ceramic which is provided for manufacturing the ceramic dental restorations according to the invention comprises by way of components

| | |
|---|---|
| 40–95 wt.-% | $SiO_2$ |
| 5–25 wt.-% | $Al_2O_3$ |
| 5–25 wt.-% | $K_2O$ |
| 0–25 wt.-% | $Na_2O$ |
| 0–20 wt.-% | CaO |
| 0–8 wt.-% | $B_2O_3$ |
| 0–0.5 wt.-% | $P_2O_5$ |
| 0–3 wt.-% | F. |

The glass-ceramic may contain by way of further components

| | |
|---|---|
| 0–10 wt.-% | $La_2O_3$ |
| 0–10 wt.-% | $Sb_2O_3$ |
| 0–10 wt.-% | $Li_2O$ |
| 0–20 wt.-% | MgO |
| 0–20 wt.-% | BaO |
| 0–20 wt.-% | SrO |
| 0–3.5 wt.-% | ZnO |
| 0–30 wt.-% | $TiO_2$ |
| 0–14 wt.-% | $ZrO_2$ |
| 0–30 wt.-% | $CeO_2$ |
| 0–30 wt.-% | $SnO_2$. |

The glass-ceramic preferably comprises:

| | |
|---|---|
| 50–80 wt.-% | $SiO_2$ |
| 12–25 wt.-% | $Al_2O_3$ |
| 7–18 wt.-% | $K_2O$ |
| 0.5–25 wt.-% | $Na_2O$ |
| 0.1–2.5 wt.-% | CaO. |

By virtue of this composition it is established that the glass-ceramic which has been processed into the dental product contains, as sole crystalline phase, leucite in a total proportion from 20 to 45 wt.-% and that it consequently exhibits a linear coefficient of thermal expansion $\alpha_{(20\text{-}500°\ C.)}$ from $12.5\cdot10^{-6}$ to $15.5\cdot10^{-6}\ K^{-1}$. In this case at least 80% of the theoretically producible quantity of leucite is present in the glass-ceramic. By virtue of is the virtually quantitative formation of the leucite phase it is further established that in the course of subsequent thermal treatment, such as, in particular, the application of facing-ceramic, no significant change in the leucite content arises and hence no drifting of the CTE of the basic glass-ceramic towards higher CTE values. The glass-ceramic preferably contains 35 to 40 wt.-% leucite, the latter having been formed in a proportion constituting at least 90% of the theoretically producible quantity; this material then has a CTE $\alpha_{(20\text{-}500°\ C.)}$ from $13.0\cdot10^{-6}$ to $14.0\cdot10^{-6}\ K^{-1}$.

With a material of this type it is accordingly possible for dental objects based on glass-ceramic to be manufactured selectively, the CTE of which lies below that of the conventional dental facing-ceramics and also does not change towards higher values.

DETAILED DESCRIPTION OF THE INVENTION

The ceramic dental restoration according to the invention is found to be excellent for facing with currently available dental facing-ceramics having a linear coefficient of thermal expansion $\alpha_{(20\text{-}500°\ C.)}$ from $13.5\cdot10^{-6}$ to $17.0\cdot10^{-6}\ K^{-1}$. In this connection the CTE of the basic glass-ceramic is chosen so that it lies $0.5\cdot10^{-6}$ to $2.5\cdot10^{-6}\ K^{-1}$, preferably about $1.5\cdot10^{-6}\ K^{-1}$, below that of the facing-ceramic. Particularly preferred is a ceramic dental restoration of this type in which the linear coefficient of thermal expansion $\alpha_{(20\text{-}500°\ C.)}$ of the base ceramic amounts to $13.0\cdot10^{-6}$ to $14.0\cdot10^{-6}\ K^{-1}$ and the linear coefficient of thermal expansion $\alpha_{(20\text{-}500°\ C.)}$ of the facing-ceramic amounts to about $15.0\cdot10^{-6}\ K^{-1}$.

The process for manufacturing the ceramic dental restoration according to the invention based on leucitic glass-ceramic is effected in such a manner that (a) a primary glass or a primary glass-ceramic is produced in the form of a powder or a granulate which comprises by way of components

| | |
|---|---|
| 40–95 wt.-% | $SiO_2$ |
| 5–25 wt.-% | $Al_2O_3$ |
| 5–25 wt.-% | $K_2O$ |
| 0–25 wt.-% | $Na_2O$ |
| 0–20 wt.-% | CaO |
| 0–8 wt.-% | $B_2O_3$ |
| 0–0.5 wt.-% | $P_2O_5$ |
| 0–3 wt.-% | F, |

(b) a sintered compact in cylinder or pellet form is produced from the powder or granulate, (c) the sintered compact is converted into the viscous state at a temperature between 850 and 1,200° C. and is press-moulded under a pressure between 2 and 6 bar into a shape corresponding to the dental restoration.

As a result a glass-ceramic is formed which contains, as sole crystalline phase, leucite in a total proportion from 20 to 45 wt.-%, at least 80% of the theoretically producible quantity of leucite being present, and which exhibits a linear coefficient of thermal expansion $\alpha_{(20\text{-}500°\ C.)}$ from $12.5\cdot10^{-6}$ to $15.5\cdot10^{-6}\ K^{-1}$.

In process step (a) the stated components are mixed, melted down to form a glass, and the glass melt is then fritted in water. If desired, there may be added by way of further components:

| | |
|---|---|
| 0–10 wt.-% | $La_2O_3$ |
| 0–10 wt.-% | $Sb_2O_3$ |
| 0–10 wt.-% | $Li_2O$ |
| 0–20 wt.-% | MgO |
| 0–20 wt.-% | BaO |
| 0–20 wt.-% | SrO |
| 0–3.5 wt.-% | ZnO |
| 0–30 wt.-% | $TiO_2$ |
| 0–14 wt.-% | $ZrO_2$ |
| 0–30 wt.-% | $CeO_2$ |
| 0–30 wt.-% | $SnO_2$. |

The primary glass preferably comprises:

| | |
|---|---|
| 50–80 wt.-% | $SiO_2$ |
| 12–25 wt.-% | $Al_2O_3$ |
| 7–18 wt.-% | $K_2O$ |
| 0.5–25 wt.-% | $Na_2O$ |
| 0.1–2.5 wt.-% | CaO. |

The glass powder obtained by fritting may be ground down further and graded to a definite particle size; 100 μm is expedient. With a view to achieving extremely high homogeneity of the glass, the operation of melting down, fritting, grinding down and grading may be repeated several times. Normally the primary glass does not yet exhibit any leucite phase after these operations. But by means of any subsequent thermal treatments, for instance in the course of further processing to form initial or intermediate products for the actual manufacture of dental products, a conversion into a primary glass-ceramic may be effected by partial crystallization. The primary glass or the primary glass-ceramic may also be present in the form of granulate.

In process step (b) a sintered compact in cylinder or pellet form is produced from the powder or granulate of the primary glass or of the primary glass-ceramic. To this end the material is press-moulded to form appropriate mouldings under a pressure from 40 to 200 bar and is sintered at temperatures between 750 and 950° C. over a period from 1 to 5 minutes. With a view to application as pressed ceramic the sintered compacts are expediently dimensioned as circular blanks with a diameter of 10 to 12 mm and a height of 8 to 12 mm.

In process step (c) the processing of the sintered compact to form the shaped ceramic dental restoration is effected by press-moulding in the viscous state. In this connection the concluding conversion into a glass-ceramic is effected by crystallization of the leucite phase. Processing may be effected substantially in accordance with the process and in a pressing furnace as are described in EP 0 231 773 A1 which is relied on and incorporated herein by reference.

Production of the mould for the dental restoration, which is necessary to begin with, is effected using the conventional technology of wax modelling, embedding of the wax model which is provided with a sprue in a commercially available self-hardening fireproof embedding mass and expulsion of the wax by heating. The mould is introduced into the pressing furnace, the correspondingly dimensioned sprue is equipped with the sintered compact made of primary glass or primary glass-ceramic, said sintered compact is converted into the viscous state at a temperature between 950 and 1,200° C. and is press-moulded into shape under a pressure between 2 and 6 bar. In the course of this operation, crystallization is effected of at least 80% of the theoretically producible quantity of leucite, which is then present in the glass-ceramic as sole crystalline phase in a total proportion from 20 to 45 wt.-%. As a result of this, the glass-ceramic exhibits a linear coefficient of thermal expansion $\alpha_{(20-500°\,C.)}$ from $12.5 \cdot 10^{-6}$ to $15.5 \cdot 10^{-6}$ K$^{-1}$.

The glass-ceramic according to the invention can be readily converted into the viscous state at a temperature between 900 and 1,050° C. and press-moulded under a pressure between 3 and 5 bar. The pressing operation is normally concluded after a period of 20 minutes. After cooling, removal from the mould and removal of the sprue slug, the moulded ceramic dental restoration is present and can then be subjected to the subsequent or concluding treatments which are optionally required. These include, in particular, facing with a dental ceramic that exhibits a CTE from $13.5 \cdot 10^{-6}$ to $17.0 \cdot 10^{-6}$ K$^{-1}$, the CTE of the base ceramic being chosen so that it lies $0.5 \cdot 10^{-6}$ to $2.5 \cdot 10^{-6}$ K$^{-1}$, preferably about $1.5 \cdot 10^{-6}$ K$^{-1}$, below that of the facing-ceramic.

The ceramic dental restoration according to the invention satisfies in outstanding manner all the demands, particularly with regard to mechanical and optical properties, that are made of such products. By varying the components of the glass-ceramic within the specified ranges, the optical properties in particular, such as pigmentation, translucence and opaqueness, can be influenced.

Even though the glass-ceramic according to the invention is ideally suitable for processing as pressed ceramic, it can also be processed in accordance with other technologies to form moulded dental products with an equivalent result. Such processing technologies are shaping using slip technology and sintering, mould casting of the glass melt, compression moulding and sintering, casting or sintering to form a blank and subsequent mechanical shaping. The crystallization of leucite is effected in these cases in the sintering step or in an annealing step.

EXAMPLES 1–9

The components according to the following Table 1 are mixed homogeneously in the form of powder, melted down at a temperature of 1,550–1,600° C. to form a glass flux, and the melts are fritted in cold water. The glass powders obtained are ground down in a ball mill and sieved to a particle size of 100 μm. The glass powders are processed by press-moulding at 100 bar and sintering at 850° C. over a period of 1 min. to form sintered compacts with a diameter of 11.9 mm and a height of 10 mm. The sintered compacts are then processed in a pressing furnace according to EP 0 231 773 A1 under a pressing pressure of 3–5 bar within 1 min. to form glass-ceramic mouldings (test specimens). Table 1 shows for the respective compositions, the pressing temperature $T_p$ and the CTE of the resulting glass-ceramic. The CTE of the glass-ceramics lies between $12.5 \cdot 10^{-6}$ and $15.5 \cdot 10^{-6}$ K$^{-1}$.

TABLE 1

| No. | Composition [wt. %] | | | | | | | | | | $T_p$ [° C.] | CTE $\alpha$ (20–500° C.) $10^{-6}$ K$^{-1}$ |
|---|---|---|---|---|---|---|---|---|---|---|---|---|
| | SiO$_2$ | Al$_2$O$_3$ | K$_2$O | Na$_2$O | Li$_2$O | B$_2$O$_3$ | CaO | CeO$_2$ | Sb$_2$O$_3$ | F | | |
| 1. | 65.3 | 15.7 | 14.7 | 0.9 | — | 0.9 | 1.6 | — | — | 0.9 | 1090 | 12.5 |
| 2. | 65.0 | 15.6 | 14.7 | 0.9 | 0.4 | 0.9 | 1.6 | — | — | 0.9 | 1060 | 14.3 |
| 3. | 64.8 | 16.5 | 15.3 | 1.9 | 0.5 | — | 0.7 | — | 0.2 | 0.1 | 1150 | 15.4 |
| 4. | 56.5 | 20.0 | 11.2 | 10.5 | — | 1.0 | 0.1 | 0.7 | — | — | 900 | 15.5 |
| 5. | 58.6 | 21.5 | 10.4 | 9.4 | — | — | 0.1 | — | — | — | 1100 | 15.3 |
| 6. | 58.1 | 22.0 | 9.4 | 10.4 | — | — | 0.1– | — | — | — | 1050 | 14.0 |
| 7. | 57.8 | 22.2 | 8.9 | 11.0 | — | — | 0.1 | — | — | — | 1020 | 13.1 |
| 8. | 59.6 | 22.2 | 9.5 | 8.6 | — | — | 0.1 | — | — | — | 1160 | 13.0 |
| 9. | 59.4 | 21.6 | 10.4 | 8.5 | — | — | 0.1 | — | — | — | 1120 | 15.3 |

EXAMPLE 10

Sintered compacts with the composition according to Example 7 are processed as described above at differing pressing temperatures to form dental mouldings (crowns).

After this, the crowns are faced with a commercially available facing-ceramic (Duceragold®, manufactured by Ducera) in accordance with the manufacturer's instructions. With a view to testing for thermal-shock resistance, the crowns are chilled after each firing (a total of five firings) by being taken out of boiling water and placed in water at room temperature ($\Delta T=80°$ C.) and are examined for cracking. Table 2 shows the CTE of the dental mouldings, which, depending on the pressing temperature, amounts to between $13.1 \cdot 10^{-6}$ and $13.8 \cdot 10^{-6}$ $K^{-1}$, after the pressing operation and the CTE difference relative to the facing-ceramic after 1–5 firings, depending on the change in CTE (towards higher values) of the facing-ceramic. Table 2 further shows the respective number of crowns examined in the thermal-shock test and the number of defective crowns in this connection. The result of the thermal-shock test is excellent in the $\Delta$CTE range $0.5$–$2.5 \cdot 10^{-6}$ $K^{-1}$.

Further variations and modifications of the foregoing will be apparent to those skilled in the art and are intended to be encompassed by the claims appended hereto.

German priority application 198 52 516.8 is relied on and incorporated herein by reference.

TABLE 2

| Pressing temperature $T_P$ [° C.] | Pressed ceramic CTE $\alpha_{(20-500° C.)}$ [$10^{-6}$ $K^{-1}$] (drift-stable in subsequent firings) | CTE difference relative to the facing-ceramic: period between 1st and 5th firing. | Tested crowns | Crowns with fracture (after number of firings) |
|---|---|---|---|---|
| 1040 | 13.0 | 0.9–2.4 | 10 | 1 (after 3rd firing) |
| 990 | 13.3 | 0.6–2.1 | 10 | 0 |
| 940 | 13.7 | 0.2–1.7 | 10 | 8 (after 1st firing) |
| 990 | 13.3 | 2.6 | 3 | 3 (after 1st * firing) |

* Comparative experiment: experimental batch of a facing-ceramic with a CTE $\alpha_{(20-500° C.)}$ of 15.9.

What is claimed is:

1. A molded ceramic dental restoration comprising a ceramic base faced with a dental facing ceramic wherein said ceramic base is a leucitic glass-ceramic, comprising

| 40–95 wt.-% | $SiO_2$ |
|---|---|
| 5–25 wt.-% | $Al_2O_3$ |
| 5–25 wt.-% | $K_2O$ |
| 0–25 wt.-% | $Na_2O$ |
| 0–20 wt.-% | CaO |
| 0–8 wt.-% | $B_2O_3$ |
| 0–0.5 wt.-% | $P_2O_5$ |
| 0–3 wt.-% | F, | and containing, as the sole crystalline phase, leucite in a total proportion from 20 to 45 wt.-%, at least 80% of the theoretically producible quantity of leucite being present, and in which glass ceramic exhibits a linear coefficient of thermal expansion $\alpha_{(20-500° C.)}$ from $12.5 \cdot 10^{-6}$ to $15.5 \cdot 10^{-6}$ $K^{-1}$, and wherein said dental ceramic exhibits a linear coefficient of thermal expansion $\alpha_{(20-500° C.)}$ from $13.5 \cdot 10^{-6}$ to $17.0 \cdot 10^{-6}$ $K^{-1}$, the coefficient thermal expansion of said glass ceramic being chosen so that lies $0.5 \cdot 10^{-6}$ to $2.5 \cdot 10^{-6}$ $K^{-1}$ below that of the facing-ceramic.

2. The molded ceramic dental restoration according to claim 1, wherein the glass-ceramic further comprises

| 0–10 wt.-% | $La_2O_3$ |
|---|---|
| 0–10 wt.-% | $Sb_2O_3$ |
| 0–10 wt.-% | $Li_2O$ |
| 0–20 wt.-% | MgO |
| 0–20 wt.-% | BaO |
| 0–20 wt.-% | SrO |
| 0–3.5 wt.-% | ZnO |
| 0–30 wt.-% | $TiO_2$ |
| 0–14 wt.-% | $ZrO_2$ |
| 0–30 wt.-% | $CeO_2$ |
| 0–30 wt.-% | $SnO_2$. |

3. The molded ceramic dental restoration according to claim 2, wherein the coefficient of thermal expansion of said glass ceramic lies $5 \cdot 10^{-6}$ to $2.5 \cdot 10^{-6}$ $K^{-1}$ below that of the facing-ceramic.

4. The molded ceramic dental restoration according to claim 2, wherein the glass-ceramic comprises

| 50–80 wt.-% | $SiO_2$ |
|---|---|
| 12–25 wt.-% | $Al_2O_3$ |
| 7–18 wt.-% | $K_2O$ |
| 0.5–25 wt.-% | $Na_2O$ |
| 0.1–2.5 wt.-% | CaO. |

5. The molded ceramic dental restoration according to claim 4, wherein the linear coefficient of thermal expansion $\alpha_{(20-500° C.)}$ of the glass ceramic is $13.0 \cdot 10^{-6}$ to $14.0 \cdot 10^{-6}$ $K^{-1}$ and the linear coefficient of thermal expansion $\alpha_{(20-500° C.)}$ of the facing-ceramic is about $15.0 \cdot 10^{-6}$ $K^{-1}$.

6. The molded ceramic dental restoration according to claim 1, wherein the glass-ceramic comprises

| 50–80 wt.-% | $SiO_2$ |
|---|---|
| 12–25 wt.-% | $Al_2O_3$ |
| 7–18 wt.-% | $K_2O$ |
| 0.5–25 wt.-% | $Na_2O$ |
| 0.1–2.5 wt.-% | CaO. |

7. The molded ceramic dental restoration according to claim 6, wherein the coefficient of thermal expansion of said glass ceramic lies $0.5 \cdot 10^{-6}$ to $2.5 \cdot 10^{-6}$ $K^{-1}$ below that of the facing-ceramic.

8. The molded ceramic dental restoration according to claim 1, wherein the coefficient of thermal expansion of said glass ceramic lies $1.5 \cdot 10^{-6}$ K$^{-1}$ below that of the facing-ceramic.

9. A process for manufacturing a molded ceramic dental restoration formed of a base and a dental facing ceramic comprising (a) providing a primary glass or a primary glass-ceramic in the form of a powder or a granulate which comprises:

| | |
|---|---|
| 40–95 wt.-% | SiO$_2$ |
| 5–25 wt.-% | Al$_2$O$_3$ |
| 5–25 wt.-% | K$_2$O |
| 0–25 wt.-% | Na$_2$O |
| 0–20 wt.-% | CaO |
| 0–8 wt.-% | B$_2$O$_3$ |
| 0–0.5 wt.-% | P$_2$O$_5$ |
| 0–3 wt.-% | F, |

(b) forming a sintered compact in cylinder or pellet form from said power granulate, (c) converting the sintered compact into a viscous state at a temperature between 850 and 1,200° C. and press molding said sintered compact in a viscous state under a pressure between 2 and 6 bar into a shape corresponding to dental restoration, as a result of which a glass-ceramic is formed which contains, as sole crystalline phase, leucite in a total proportion of 20–45 wt.-%, at least 80% of the theoretically producible quantity of leucite being present, and which exhibits a linear coefficient of thermal expansion $\alpha_{(20-500°\ C.)}$ from $12.5 \cdot 10^{-6}$ to $15.5 \cdot 10^{-6}$ K$^{-1}$, and, further facing the dental restoration shaped into the desired form with a dental ceramic which exhibits a linear coefficient of thermal expansion $\alpha_{(20-500°\ C.)}$ from $13.5 \cdot 10^{-6}$ to $17.0 \cdot 10^{-6}$ K$^{-1}$, where the coefficient of thermal expansion of the base ceramic lies $0.5 \cdot 10^{-6}$ to $2.6 \cdot 10^{-6}$ K$^{-1}$ below that of the facing-ceramic.

10. The process according to claim 9, wherein the efficient of thermal expansion of the base ceramic lies about $1.5 \cdot 10^{-6}$ K$^{-1}$ below that of the facing-ceramic.

11. The process according to claim 9, wherein the base ceramic has a linear coefficient of thermal expansion $\alpha_{(20-500°\ C.)}$ from $13.0 \cdot 10^{-6}$ to $14.0 \cdot 10^{-6}$ K$^{-1}$ and is faced with a facing-ceramic having a linear coefficient of thermal expansion $\alpha_{(20-500°\ C.)}$ of about $15.0 \cdot 10^{-6}$ K$^{-1}$.

12. The process according to claim 9, wherein the primary glass or a primary glass-ceramic comprises as further components

| | |
|---|---|
| 0–10 wt.-% | La$_2$O$_3$ |
| 0–10 wt.-% | Sb$_2$O$_3$ |
| 0–10 wt.-% | Li$_2$O |
| 0–20 wt.-% | MgO |
| 0–20 wt.-% | BaO |
| 0–20 wt.-% | SrO |
| 0–3.5 wt.-% | ZnO |
| 0–30 wt.-% | TiO$_2$ |
| 0–14 wt.-% | ZrO$_2$ |
| 0–30 wt.-% | CeO$_2$ |
| 0–30 wt.-% | SnO$_2$. |

13. The process according to claim 12, further comprising converting the sintered compact into the viscous state at a temperature between 900 and 1,050° C. and press-moulding under a pressure between 3 and 5 bar into a shape corresponding to the dental restoration.

14. The process according to claim 9, wherein the primary glass or primary glass-ceramic comprises:

| | |
|---|---|
| 50–80 wt.-% | SiO$_2$ |
| 12–25 wt.-% | Al$_2$O$_3$ |
| 7–18 wt.-% | K$_2$O |
| 0.5–25 wt.-% | Na$_2$O |
| 0.1–2.5 wt.-% | CaO. |

15. The process according to claim 9, further comprising converting the sintered compact into the viscous state at a temperature between 900 and 1,050° C. and press-moulding under a pressure between 3 and 5 bar into a shape corresponding to the dental restoration.

\* \* \* \* \*

UNITED STATES PATENT AND TRADEMARK OFFICE
CERTIFICATE OF CORRECTION

PATENT NO. : 6,342,302 B1
DATED : January 29, 2002
INVENTOR(S) : Jurgen Steidl and Steffen Assmann It is certified that error appears in the above-identified patent and that said Letters Patent is hereby corrected as shown below:

Column 7,
Lines 62 and 63, change "dental ceramic" to -- dental facing ceramic --.

Column 8,
Line 19, change "$5 \cdot 10^{-6}$ to $2.5 \cdot 10^{-6}$ $K^{-1}$" to -- $0.5 \cdot 10^{-6}$ to $2.5 \cdot 10^{-6}$ $K^{-1}$ --

Signed and Sealed this

Thirty-first Day of December, 2002

JAMES E. ROGAN
*Director of the United States Patent and Trademark Office*